United States Patent [19]

Penco et al.

[11] 4,146,616
[45] Mar. 27, 1979

[54] ANTITUMOR COMPOUNDS, THEIR PREPARATION AND USE

[75] Inventors: Sergio Penco; Francesco Angelucci; Federico Arcamone, all of Milan, Italy

[73] Assignee: Societa Farmaceutici Italia S.p.A., Milan, Italy

[21] Appl. No.: 860,448

[22] Filed: Dec. 14, 1977

[30] Foreign Application Priority Data

Dec. 22, 1976 [GB] United Kingdom ............... 53455/76

[51] Int. Cl.² ............................................. A61K 31/70
[52] U.S. Cl. ........................................ 424/180; 536/4; 536/17
[58] Field of Search .................... 536/4 A, 17 A, 4; 424/180

[56] References Cited

U.S. PATENT DOCUMENTS 4,020,270  4/1977  Arcamone et al. ................... 536/4

Primary Examiner—Ethel G. Love

Attorney, Agent, or Firm—Hubbell, Cohen, Stiefel & Gross

[57] ABSTRACT

Disclosed are new antitumor compounds of the formula:

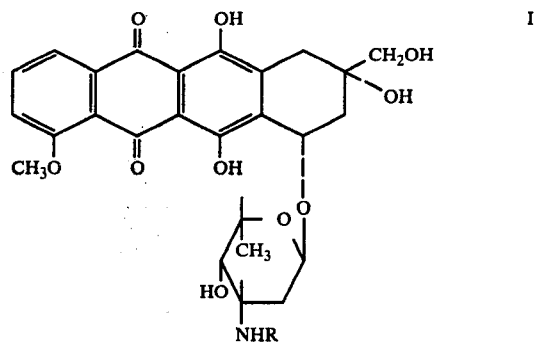

wherein R is hydrogen or trifluoroacetyl and the hydrochlorides thereof and a process for making same. Also disclosed is a novel intermediate (9-desacetyl-9-formyl-N-trifluoroacetyldaunorubicin) used in the process.

5 Claims, No Drawings

ANTITUMOR COMPOUNDS, THEIR PREPARATION AND USE

BACKGROUND OF THE INVENTION

1. Field of the Invention

The invention relates to new antitumor compounds which are daunorubicin derivatives, in particular, 9-desacetyl-9-hydroxymethyl derivatives of daunorubicin, a process for making them, as well as a key intermediate in the synthesis thereof and a method of using them in treating tumors. The invention described herein was made in the course of work under a grant from the U.S. Department of Health, Education and Welfare.

2. The Prior Art

Daunorubicin (also known as daunomycin) is a known compound which is described in British Pat. No. 1,003,383, owned by the unrecorded assignee hereof. In addition, the starting material for the process according to this invention, namely, 13-dihydrodoxorubicin, is a known compound which is described in West German patent publication (Offenlegungsschrift) No. 2,202,690.

SUMMARY OF THE INVENTION

The present invention provides, in one aspect thereof, new antitumor agents of the formula:

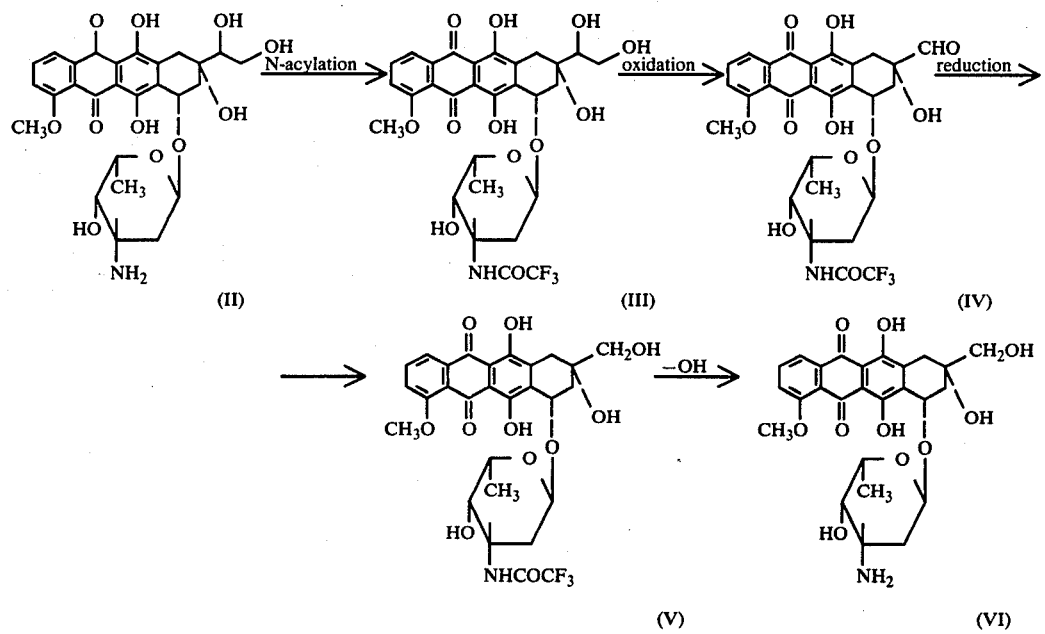

wherein R is hydrogen or trifluoroacetyl and the hydrochlorides thereof.

In another aspect, the invention provides a process for making these compounds, which process involves the use of a novel, key intermediate (9-desacetyl-9-formyl-N-trifluoroacetyldaunorubicin) which is also part of the invention. Finally, the invention provides a method of using the antitumor compounds of the invention in treating certain mammalian tumors such as lymphocytic leukemia $P_{388}$.

The process of the invention by which the compounds of formula I are synthesized is illustrated in the following scheme starting from 13-dihydrodoxorubicin (II), a known compound.

In this process, the N-acylation of compound II is performed by treatment with acid anhydrides or acyl-chlorides in aqueous acetone. More particularly, N-trifluoroacetylation is performed by treatment of II with trifluoroacetic anhydride, followed by hydrolysis of the O-trifluoroacetyl groups with methanol to form III in almost quantitative yield. The following oxidation step of the C-13, C-14 diol, is carried out in t-butyl alcohol in the presence of one equivalent of sodium periodate at room temperature. The compound IV is isolated from the reaction mixture in about 80% yield. Compound IV, upon treatment with $NaBH_3CN$ under acid conditions is converted to the corresponding alcohol in quantitative yield. The removal of the N-trifluoroacetyl group by mild alkaline treatment allows one to obtain 9-desacetyl-9-hydroxymethyldaunomycin VI, isolated as the hydrochloride. The new compounds of formula I display antimitotic activity and are therefore useful therapeutic agents for the treatment of tumor diseases in mammals.

DESCRIPTION OF THE PREFERRED EMBODIMENTS

The following examples are given to illustrate the preparation of compounds according to the invention without, however, being a limitation thereof. Unless otherwise indicated, all parts given are by weight.

EXAMPLE 1

N-Trifluoroacetyl-13-dihydrodoxorubicin III

A suspension of 4.6 g. of 13-dihydrodoxorubicin (II) in 600 ml. of chloroform was treated with 40 ml. of trifluoroacetic anhydride at 0° for one hour. The reaction mixture was evaporated to a residue under vacuum, and the resulting residue was dissolved in 200 ml. of methanol and treated with a saturated aqueous solution of sodium bicarbonate. After 30 minutes at room temperature, the solvent was eliminated under vacuum and the aqueous solution was extracted with n-butanol until the extracts were colorless. The organic phase, i.e., the combined n-butanol extracts, was washed with water, evaporated to a small volume (50 ml.) and added to excess petroleum ether to give 4.5 g. of pure N-trifluoroacetyl-13-dihydrodoxorubicin (III). Thin layer chromatography (TLC) on Kieselgel plates $F_{254}$ (Merck) using as the solvent system, $CHCl_3$—$(CH_3)_2CO$ (2:1 v/v); Rf = 0.1.

EXAMPLE 2

9-Desacetyl-9-formyl-N-trifluoroacetyldaunorubicin IV

A solution of 1.3 g. of $NaIO_4$ in 400 ml. of water was added, at room temperature, over 30 minutes to a solution of 4 g. of N-trifluoroacetyl-13-dihydrodoxorubicin (III) in 520 ml. of t-butyl alcohol. The reaction mixture was stirred for two hours, diluted with water and then extracted with chloroform. The organic phase after being washed with water and dried over $Na_2SO_4$, was evaporated to a small volume and added to excess petroleum ether to give 3.5 g. of 9-desacetyl-9-formyl-N-trifluoroacetyldaunorubicin IV. TLC on Merck Kieselgel 60 $F_{254}$ using as the solvent system, chloroform-acetone (2:1 v/v); Rf = 0.23.

EXAMPLE 3

9-Desacetyl-9-hydroxymethyldaunorubicin VI

A solution of 1.6 g. of 9-desacetyl-9-formyl-N-trifluoroacetyl daunorubicin (IV) in 320 ml. of 1,2-dimethoxyethane was adjusted to pH 3 with aqueous 0.1N HCl and treated with 0.3 g. of $NaBH_3CN$ at room temperature for 15 minutes, after which 1000 ml. of water were added to the reaction mixture and extraction with chloroform (5 × 200 ml.) was carried out. The organic phase, after being washed with water and dried over $Na_2SO_4$, was evaporated to dryness under vacuum. The residue was treated at 0° with 1000 ml. of 0.1N NaOH. After 30 minutes the pH was adjusted to 8.5 with 0.1N HCl and the solution was repeatedly extracted with chloroform. The combined chloroform extracts were dried over $Na_2SO_4$ and evaporated to a small volume (30 ml.). This solution, upon the addition of the stoichiometric amount of methanolic HCl and ether gave a red precipitate which was collected, washed with ether and dried under vacuum. There was obtained 0.9 g. of 9-desacetyl-9-hydroxymethyl daunorubicin (VI) by crystallization from dioxane-methanol, having a m.p. of 165° (dec.). TLC on Kieselgel plate $F_{254}$ (Merck) using as the solvent system $CHCl_3$—$CH_3OH$—$H_2O$ (13:6:1 v/v); Rf = 0.34.

| Elemental analysis calculated for $C_{26}H_{29}NO_{10}$ . HCl: | H 5.49; C 56.57; N 2.54; Cl 6.42 |
|---|---|
| found: | H 5.82; C 56.74; N 2.12; Cl 5.69 |

BIOLOGICAL ACTIVITY 9-desacetyl-9-hydroxymethyldaunorubicin hydrochloride (VI) was tested under the auspicies of NCI — National Institute of Health, Bethesda, Md., against Lymphocytic Leukemia $P_{388}$ according to the procedure described in Cancer Chemotherapy Reports, Part 3, volume 3, page 9 (1972). The following tables serve to illustrate the antitumor activity of this compound. Compound (VI) was compared to daunorubicin and doxorubicin by treatment of CDF, male mice infected with tumor cells: the intraperitoneal injections were made on days 5, 9 and 13 with a 4 day interval between each single injection starting from the fifth day after the tumor transplantation in the mice (Table 1).

The activity of the same compound (VI) was also tested by i.p. treatment on days 1–9 in infected CDF, female mice and CDF, male mice (Table 2).

TABLE 1

| Compound | Schedule of treatment in days (i.p.) | Dose mg./kg. | T/C % |
|---|---|---|---|
| 9-Desacetyl-9-hydroxymethyl-daunorubicin . HCl |  | 36.0 | 97 |
|  |  | 18.0 | 123 |
|  | 5,9,13 | 9.0 | 121 |
|  |  | 4.5 | 123 |
|  |  | 2.25 | 118 |
| Daunorubicin . HCl |  | 32.0 | 101 |
|  |  | 16.0 | 123 |
|  | 5,9,13 | 8.0 | 131 |
|  |  | 4.0 | 133 |
|  |  | 2.0 | 120 |
| Doxorubicin . HCl |  | 16.0 | 101 |
|  |  | 8.0 | 121 |
|  | 5,9,13 | 4.0 | 145 |
|  |  | 2.0 | 133 |
|  |  | 1.0 | 114 |

TABLE 2

| Compound | Schedule of treatment in days (i.p.) | Dose mg./kg. | T/C % |
|---|---|---|---|
| 9-Desacetyl-9-hydroxymethyl-daunorubicin . HCl |  | 6.25 | 88 |
|  | 1 to 9* | 3.13 | 167 |
|  |  | 1.56 | 183 |
|  |  | 0.78 | 167 |
|  |  | 0.39 | 137 |
|  |  | 0.20 | 135 |
| Daunorubicin . HCl |  | 3.13 | 135 |
|  |  | 1.56 | 190 |
|  | 1 to 9* | 0.78 | 189 |
|  |  | 0.39 | 172 |
|  |  | 0.20 | 149 |
| Doxorubicin . HCl |  | 3.13 | 100 |
|  |  | 1.56 | 213 |
|  | 1 to 9* | 0.78 | 201 |
|  |  | 0.39 | 189 |
|  |  | 0.20 | 165 |
| 9-Desacetyl-hydroxymethyl-daunorubicin . HCl |  | 25.0 | 0 |
|  |  | 12.5 | 0 |
|  | 1 to 9** | 6.25 | 76 |
|  |  | 3.13 | 122 |
|  |  | 1.56 | 168 |
| Daunorubicin . HCl |  | 3.13 | 92 |
|  |  | 1.56 | 183 |
|  | 1 to 9** | 0.78 | 154 |
|  |  | 0.39 | 150 |
|  |  | 0.20 | 140 |
| Doxorubicin . HCl |  | 3.13 | 68 |
|  |  | 1.56 | 122 |
|  | 1 to 9** | 0.78 | 174 |
|  |  | 0.39 | 182 |
|  |  | 0.20 | 165 |

*Test animals - CDF female mice
**Test animals - CDF male mice

Variations and modifications can, of course, be made without departing from the spirit and scope of the invention.

Having thus described our invention what we desire to secure by Letters Patent and hereby claim is:

1. A compound of the formula:

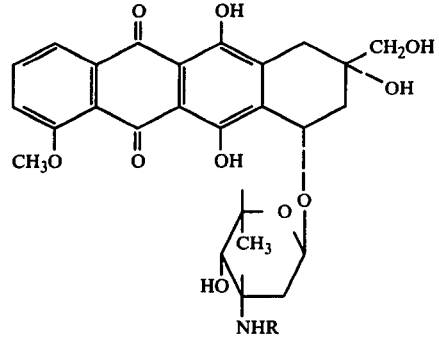

wherein R is hydrogen or trifluoroacetyl and the hydrochlorides thereof.

2. A compound according to claim 1, wherein R is hydrogen.
3. A compound according to claim 1, wherein R is trifluoroacetyl.
4. 9-Desacetyl-9-formyl-N-trifluoroacetyldaunorubicin.
5. A method of inhibiting the growth of lymphocytic leukemia $P_{388}$ which comprises intraperitoneally administering to a host afflicted therewith a compound according to claim 1 in an amount sufficient to inhibit the growth thereof.

* * * * *